United States Patent
Bloch et al.

(10) Patent No.: US 11,564,707 B2
(45) Date of Patent: Jan. 31, 2023

(54) HIGH CAPACITY HAIR FOLLICLE IMPLANT INSTRUMENT INCLUDING STAGGERED NEEDLES AND ASSOCIATED METHODS

(71) Applicant: BML Medical, LLC, Melbourne, FL (US)

(72) Inventors: Marcos David Bloch, Melbourne, FL (US); Leila David Bloch, São Paulo (BR)

(73) Assignee: BML Medical, LLC, Melbourne, FL (US)

( * ) Notice: Subject to any disclaimer, the term of this patent is extended or adjusted under 35 U.S.C. 154(b) by 535 days.

(21) Appl. No.: 16/773,140

(22) Filed: Jan. 27, 2020

(65) Prior Publication Data

US 2021/0228230 A1    Jul. 29, 2021

(51) Int. Cl.
*A61B 17/34* (2006.01)
*A61B 17/00* (2006.01)
*A61F 2/10* (2006.01)

(52) U.S. Cl.
CPC ...... *A61B 17/3403* (2013.01); *A61B 17/3468* (2013.01); *A61B 2017/00752* (2013.01); *A61B 2017/3409* (2013.01); *A61F 2/10* (2013.01)

(58) Field of Classification Search
CPC ... A61F 2/10; A61B 17/3468; A61B 17/3403; A61B 2017/3409; A61B 2017/00752
See application file for complete search history.

(56) References Cited

U.S. PATENT DOCUMENTS

| | | | | |
|---|---|---|---|---|
| 3,596,292 A | * | 8/1971 | Erb | A61F 2/10 606/187 |
| 2016/0120574 A1 | * | 5/2016 | Shiao | A61F 2/10 606/187 |

FOREIGN PATENT DOCUMENTS

| | | | | |
|---|---|---|---|---|
| FR | 2715823 A1 | * | 8/1995 | ......... A61B 17/3468 |
| KR | 200473555 Y1 | * | 7/2014 | ............... A61F 2/10 |

* cited by examiner

*Primary Examiner* — Tuan V Nguyen
(74) *Attorney, Agent, or Firm* — Mark Malek; Jonathan Staudt; Widerman Malek, PL

(57) ABSTRACT

A hair follicle implant device includes a needle holding assembly configured to hold a plurality of needles and a needle guide slidably coupled thereto and configured to provide a skin stop surface while guiding the plurality needles. A plurality of pistons is configured to slide within a respective one of the plurality of needles. A piston base is slidably coupled to the needle holding assembly and is configured to hold the pistons to slide within the plurality of needles when actuated during implantation. A spring, carried between the needle holding assembly and the piston base, is configured to bias the piston base in a retracted position, wherein the spring is offset from a central axis of the piston base. The needle holder holds the plurality of needles in the staggered arrangement offset from the central axis of the piston base.

20 Claims, 14 Drawing Sheets

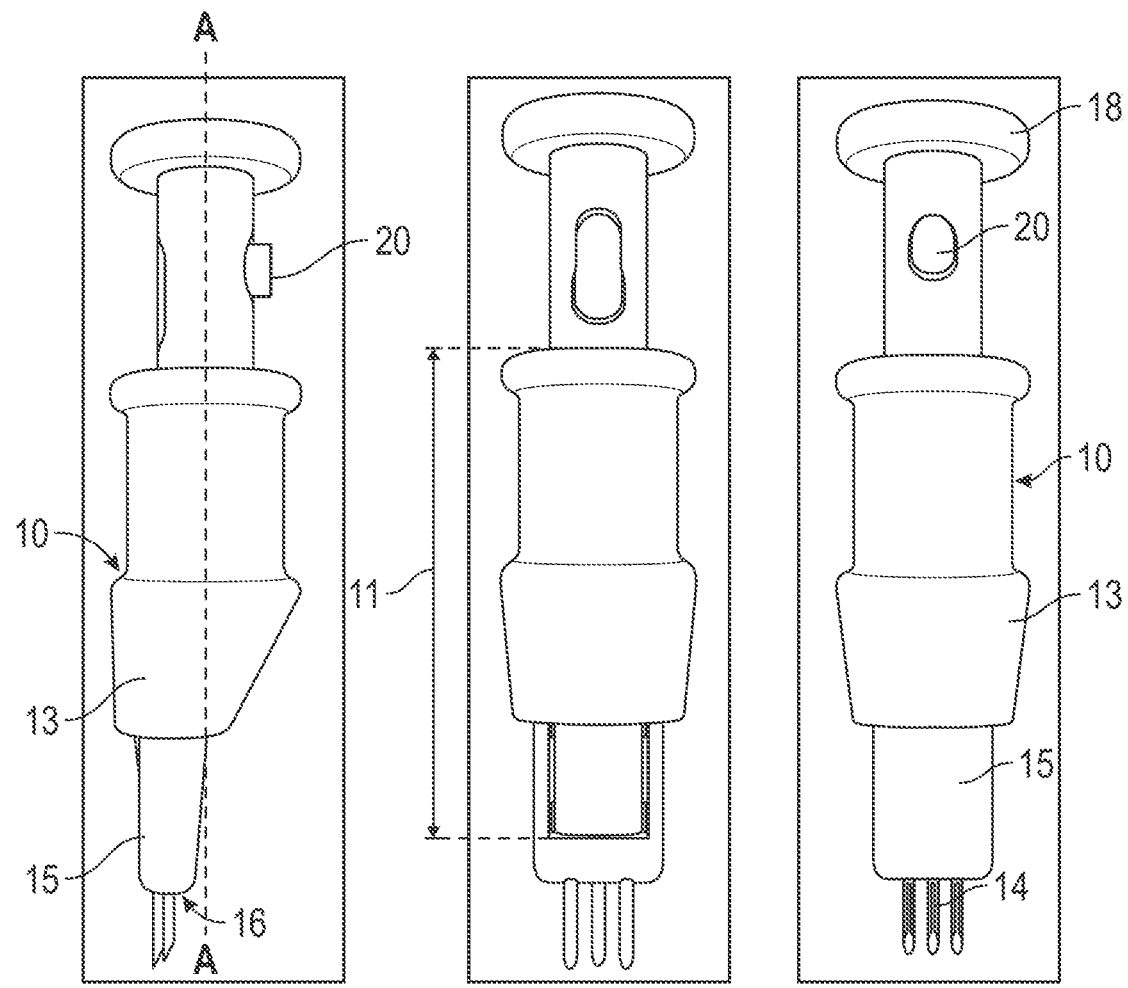
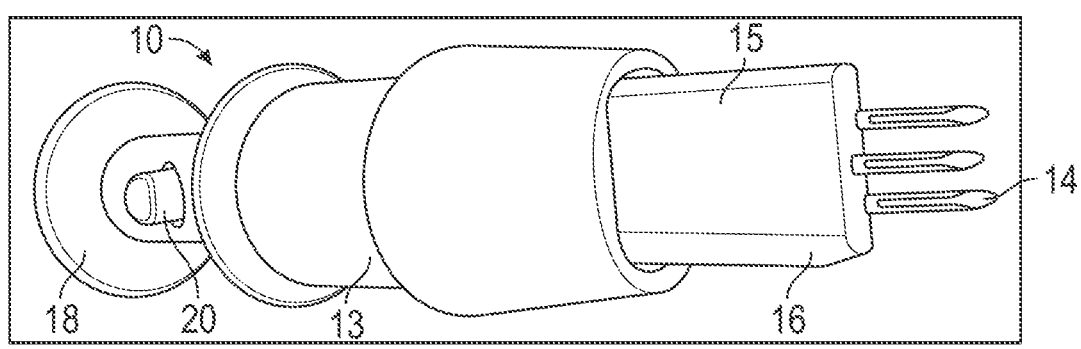

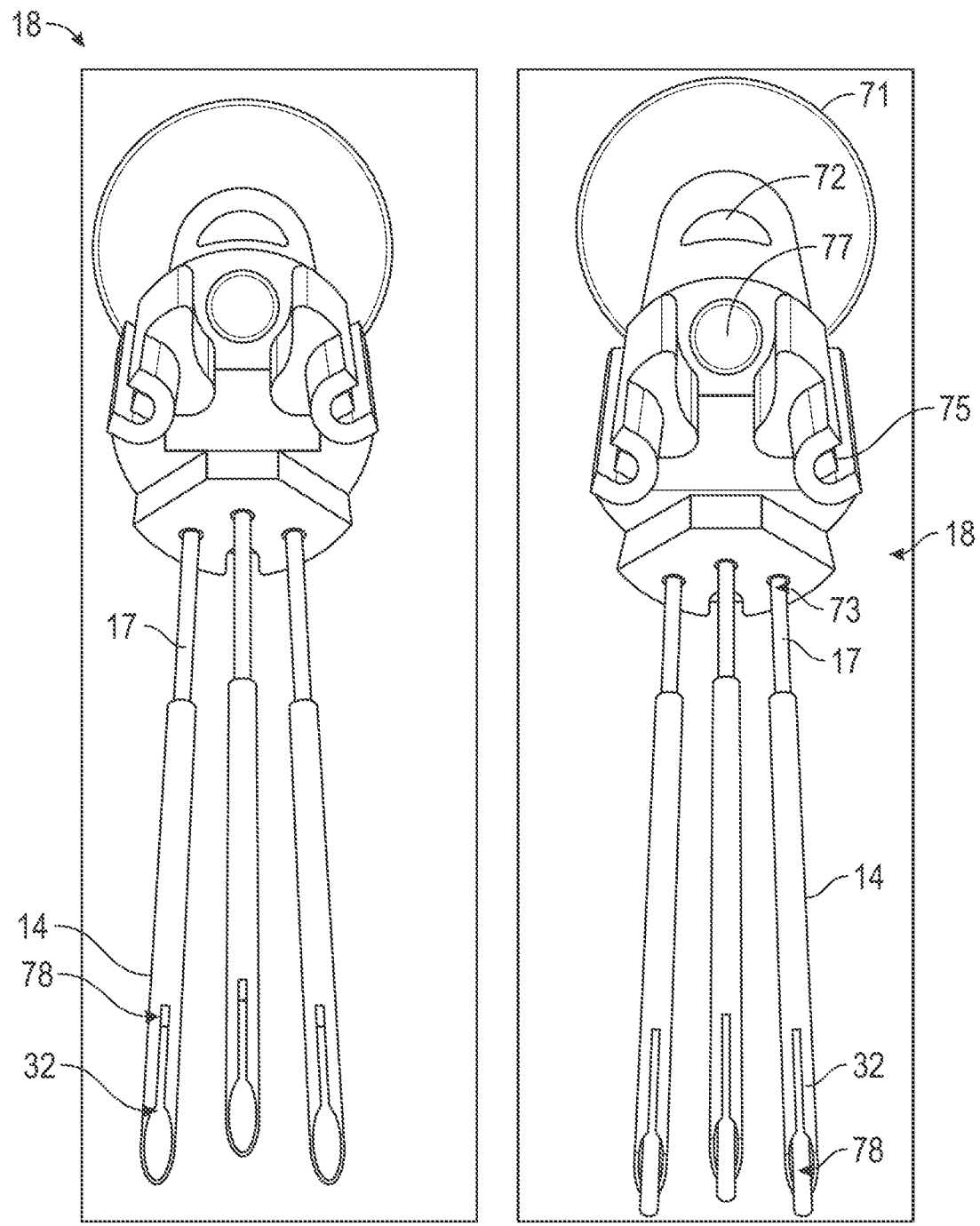

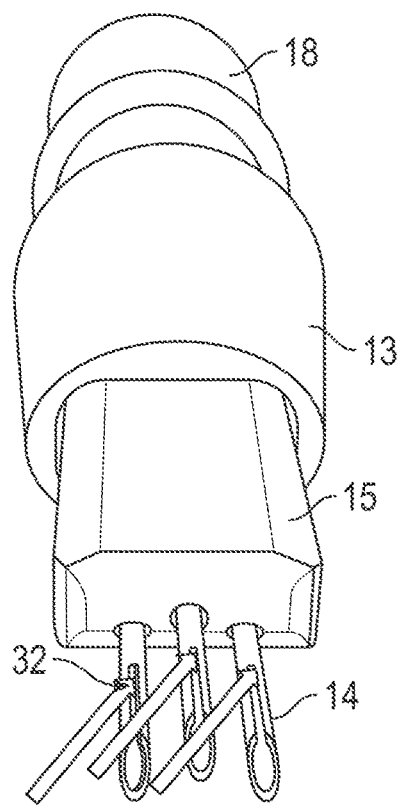
FIG. 11A
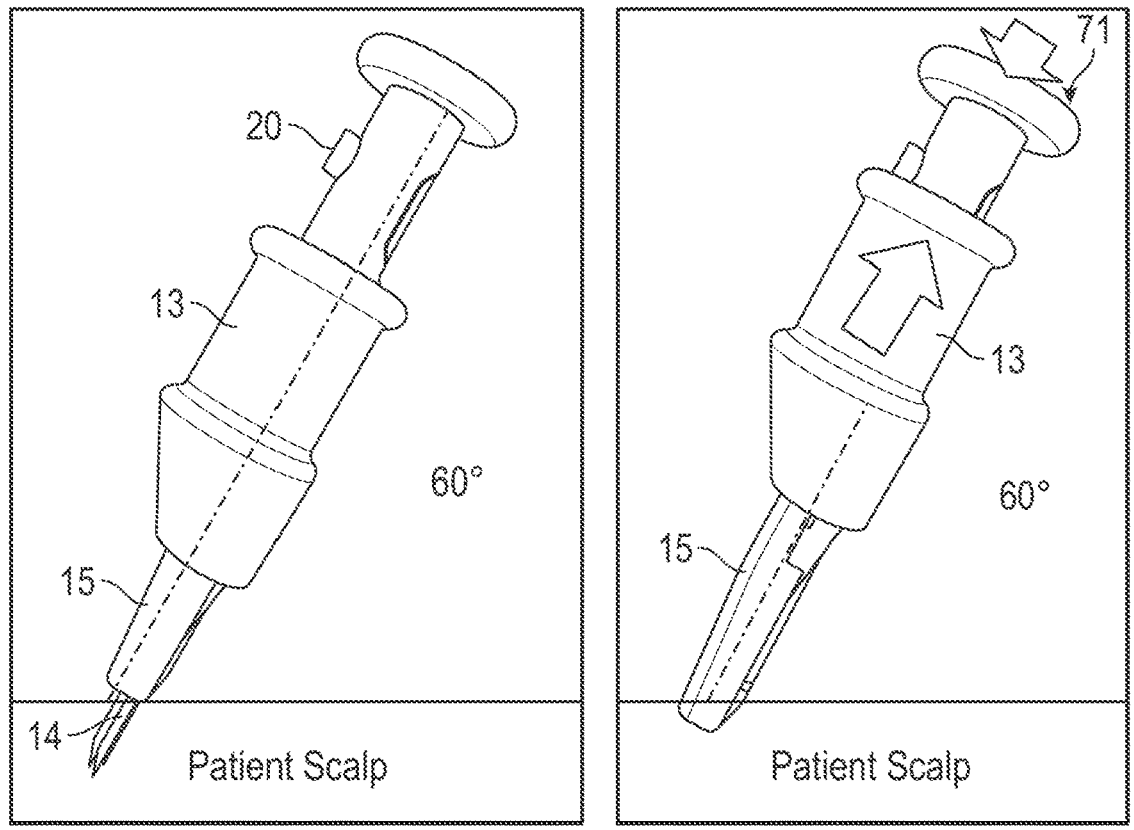
FIG. 11B
FIG. 11C

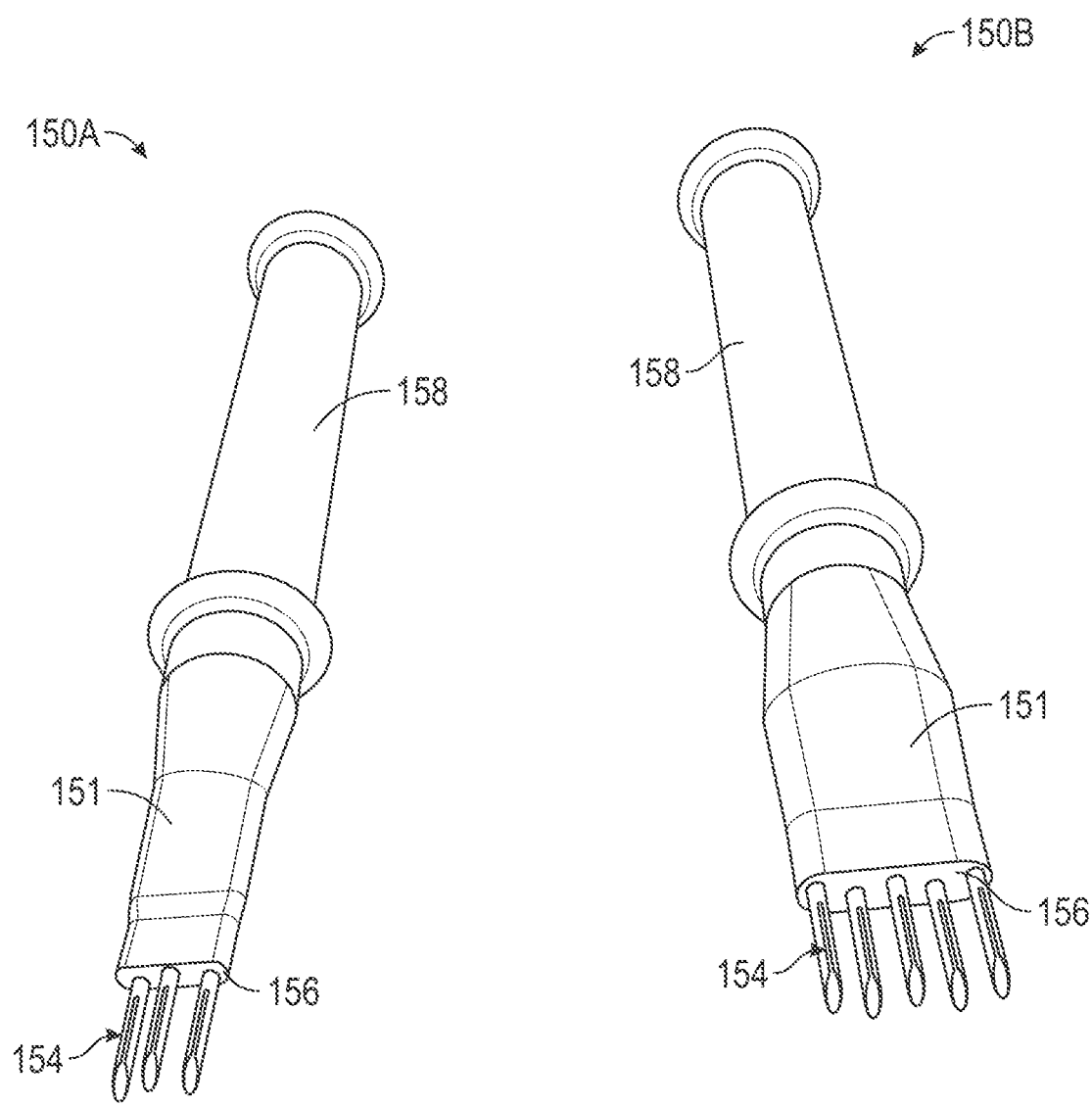

HIGH CAPACITY HAIR FOLLICLE IMPLANT INSTRUMENT INCLUDING STAGGERED NEEDLES AND ASSOCIATED METHODS

FIELD OF THE INVENTION

The present invention generally relates to instruments, devices and methods, such as hair transplantation instruments, devices and associated methods. In particular, the embodiments relate to an instrument and method for implanting hair follicular units or hair grafts, in a body surface, for example, a scalp.

BACKGROUND OF THE INVENTION

Hair follicle transplantation is a known surgical technique. A variety of restorative approaches have been used to deal with problems of baldness due to hair loss including using hair pieces, topical application, oral medication, scalp reduction, scalp flaps and hair transplantation. However, the goal continues to be to provide affordable long lasting or permanent solutions without side effect for natural looks with minimal maintenance.

Follicular hair transplantation is now widely accepted as the best restorative procedure. Clinical studies have revealed that when longer lasting hair from back and side of scalp are transplanted over the area of baldness, hair continues to stay viable and grow.

A typical hair transplantation procedure includes three steps wherein the first step involves the harvesting of hair roots from the permanent zone, the second step involving their separation and the third step in which the individual roots are planted in the desired area.

U.S. Pat. No. 5,269,801 to Shiau discloses an instrument for carrying out hair transplants. The patent discloses a device for implanting hair-containing grafts, including a guiding tube for receiving a single graft and a pushing stick inserted through one end of the guiding tube. The guiding tube is formed of a rolled plastic sheet such that the longitudinal edges overlap each other, and one end of the tube forms an inclined surface which is adapted to be inserted into a slit hole formed in the scalp of a patient. Only one graft is provided in the tube at a time and the graft is forced into the incision (slit hole) via the pushing stick. Downward movement of the pushing stick enlarges the incision due to slight outward expansion of the guiding tube.

U.S. Pat. No. 5,417,683 to Shiao is directed to a mini-graft hair implanting device for implanting multiple clumps of hair follicles at one time includes a barrel, a plunger and a depth control unit. The barrel is formed as a hollow cylinder with an open top and a bottom wall that has a cluster of hollow needles which are attached thereto so as to extend downwardly therefrom. Each of the hollow needles is adapted to receive a clump of hair follicles therein and has two open ends, a distal one of which is tapered so as to form a pointed tip. The plunger extends slidably into the barrel and has a bottom end that is formed with a set of downwardly extending first push rods and at least one downwardly extending second push rod. The first push rods are aligned with and extend into the hollow needles. The depth control unit is attached to and extends downwardly from the bottom wall of the barrel. The depth control unit includes at least one tube which is shorter than the hollow needles and which has two open ends, a distal one of which is blunt. Each second push rod is aligned with and extends into a corresponding tube.

The reduction of the hair implant surgery cycle time is a goal of the medical community that may include benefits to surgeons such as reduced total surgery cycle, increasing the number of surgeries that may be performed in a day and reduced fatigue to the surgeon. Patients would also benefit with less sedation time, improved safety and lower risk of complications.

There is a need to provide the same coverage and density as current state of the art implanters, while reducing surgeon's workload and reducing the surgery time cycle.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention are related to a hair follicle implant instrument or tool for implanting hair follicles into skin. The hair follicle implant instrument includes a needle holding assembly configured to hold a plurality of needles, including at least three implant needles, in a staggered arrangement. A needle guide, slidably coupled to the needle holding assembly, is configured to provide a skin stop surface while guiding the plurality needles in the staggered arrangement during implantation of hair follicles into the skin. A plurality of pistons, e.g. three or more pistons, are configured to slide within a respective one of the plurality of needles and hold a corresponding hair follicle in the skin while the plurality of needles is retracted from the skin. A piston base, slidably coupled to the needle holding assembly, is configured to hold the pistons in a corresponding staggered arrangement to slide within the plurality of needles when actuated during implantation of hair follicles into the skin. A spring, carried between the needle holding assembly and the piston base, is configured to bias the piston base in a retracted position, wherein the spring is offset from a central axis of the piston base. The needle holder holds the plurality of needles in the staggered arrangement offset from the central axis of the piston base.

Additionally, and/or alternatively, the needle holding assembly includes a needle base configured to hold the plurality of needles in the staggered arrangement, and a needle holder configured to hold the needle base and to be held by a hair follicle implant surgeon, during implantation, in a fixed position with the needle guide being slidably actuated relative thereto via the piston base.

Additionally, and/or alternatively, the needle base includes piston passages therein configured to permit passage of each piston within the corresponding needle.

Additionally, and/or alternatively, the piston passages are elliptical cone passages allowing a fast fitting of the pistons into the needle base to support a quick change of needles during surgery if needed.

Additionally, and/or alternatively, the needle base includes at least one guide member; and wherein the needle guide includes at least one guide rail configured to interface with the guide member of the needle base and guide relative movement therebetween.

Additionally, and/or alternatively, the needle base includes a locking member configured to lock the needle base to the needle holder and prevent relative movement therebetween during implantation.

Additionally, and/or alternatively, a needle adjustment device, carried by the piston base, is configured to adjustably couple the piston base to the needle guide for simultaneous movement relative to the needle holding assembly during implantation. The needle guide may include an adjustment interface, at an opposite end from the skin stop surface, and configured to engage the needle adjustment device. The adjustment device and the adjustment interface together may define a quick-release mechanism configured to provide for the removal and installation of the needle base from/on the needle holder.

Embodiments of the present invention are also related to a method of making a hair follicle implant instrument for implanting hair follicles into skin. The method includes: providing a needle holding assembly to hold a plurality of needles, including at least three implant needles, in a staggered arrangement; slidably coupling a needle guide to the needle holding assembly, the needle guide providing a skin stop surface while guiding the plurality needles in the staggered arrangement during implantation of hair follicles into the skin; sliding a plurality of pistons, comprising at least three pistons, into each one of the plurality of needles to hold a corresponding hair follicle in the skin while the plurality of needles is retracted from the skin; holding the pistons with a piston base in a corresponding staggered arrangement, and slidably coupling the piston base to the needle holding assembly so that the pistons slide within the plurality of needles when actuated during implantation of hair follicles into the skin; and biasing the piston base in a retracted position with a spring carried between the needle holding assembly and the piston base, wherein the spring is offset from a central axis of the piston base; wherein the needle holder assembly holds the plurality of needles in the staggered arrangement offset from the central axis of the piston base.

Additionally, and/or alternatively, the needle holding assembly includes a needle base configured to hold the plurality of needles in the staggered arrangement, and a needle holder configured to hold the needle base and to be held by a hair follicle implant surgeon, during implantation, in a fixed position with the needle guide being slidably actuated relative thereto via the piston base.

Additionally, and/or alternatively, the needle base includes piston passages therein configured to permit passage of each piston within the corresponding needle.

Additionally, and/or alternatively, the piston passages comprise elliptical cone piston passages allowing a fast fitting of the pistons into the needle base to support a quick change of needles during surgery if required.

Additionally, and/or alternatively, the needle base includes at least one guide member; and wherein the needle guide includes at least one guide rail configured to interface with the guide member of the needle base and guide relative movement therebetween.

Additionally, and/or alternatively, the needle base includes a locking member configured to lock the needle base to the needle holder and prevent relative movement therebetween during implantation.

Additionally, and/or alternatively, the method includes providing a needle adjustment device, carried by the piston base, to adjustably couple the piston base to the needle guide for simultaneous movement relative to the needle holding assembly during implantation. The needle guide may include an adjustment interface, at an opposite end from the skin stop surface, and configured to engage the needle adjustment device. The adjustment device and the adjustment interface together define a quick-release mechanism configured to provide for the removal from, and installation on, the needle holder.

BRIEF DESCRIPTION OF THE DRAWINGS

Some embodiments of the present invention are illustrated as an example and are not limited by the figures of the accompanying drawings, in which like references may indicate similar elements.

FIG. 1A is a side view of a high capacity implanter (HCI) according to an embodiment of the present invention.
FIG. 1B is a bottom view of the HCI of FIG. 1A.
FIG. 1C is a top view of the HCI of FIG. 1A.
FIG. 1D is a perspective view of the HCI of FIG. 1A.
FIG. 8A is a front perspective view of the piston base illustrating pistons retracted within respective needles for the HCI of FIGS. 1A-1D.
FIG. 8B is a front view of the piston base illustrating pistons advanced within respective needles for the HCI of FIGS. 1A-1D.
FIGS. 11A-11C are perspective views illustrating the follicular unit (FU) implant operation for the HCI of FIGS. 1A-1D.

FIGS. 15A and 15B are perspective views of alternative embodiments illustrating staggered needle arrangements for a pre-implant multi-incision modality.

DETAILED DESCRIPTION OF THE INVENTION

Figure 2:
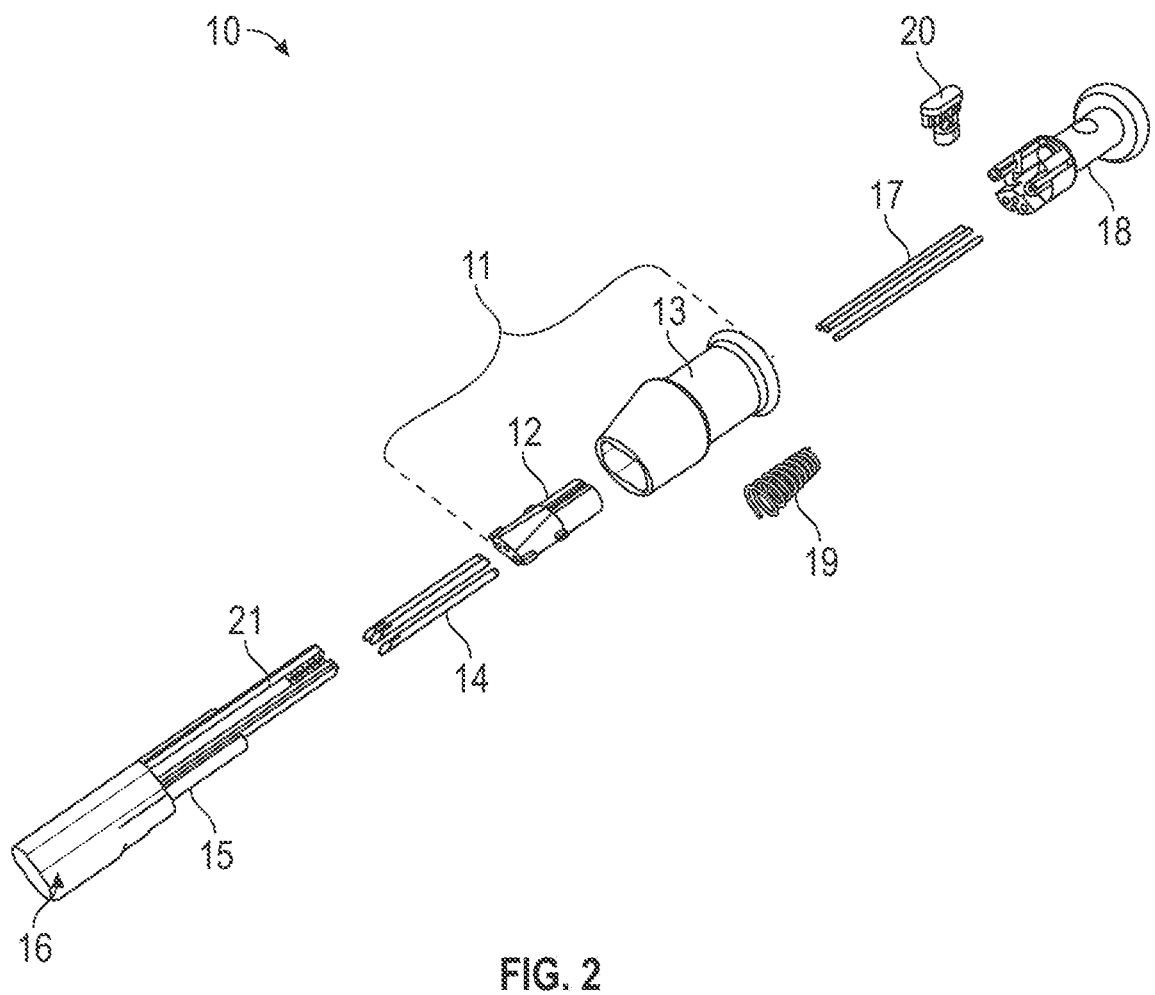
FIG. 2 is an exploded view of the HCI of FIGS. 1A-1D.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the invention.

Before describing the present disclosure in detail, it is to be understood that this disclosure is not limited to parameters of the particularly exemplified systems, methods, apparatus, products, processes, and/or kits, which may, of course, vary. It is also to be understood that the terminology used herein is only for the purpose of describing particular embodiments of the present disclosure and is not necessarily intended to limit the scope of the disclosure in any particular manner. Thus, while the present disclosure will be described in detail with reference to specific embodiments, features, aspects, configurations, etc., the descriptions are illustrative and are not to be construed as limiting the scope of the claimed invention. Various modifications can be made to the illustrated embodiments, features, aspects, configurations, etc. without departing from the spirit and scope of the invention as defined by the claims. Thus, while various aspects and embodiments have been disclosed herein, other aspects and embodiments are contemplated.

Unless defined otherwise, all technical and scientific terms used herein have the same meaning as commonly understood by one of ordinary skill in the art to which the present disclosure pertains. While several methods and materials similar or equivalent to those described herein can be used in the practice of the present disclosure, only certain exemplary materials and methods are described herein.

Various aspects of the present disclosure, including devices, systems, methods, etc., may be illustrated with reference to one or more exemplary embodiments or implementations. As used herein, the terms "embodiment," "alternative embodiment" and/or "exemplary implementation" means "serving as an example, instance, or illustration," and should not necessarily be construed as preferred or advantageous over other embodiments or implementations disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an" and "the" include plural referents unless the content clearly dictates otherwise. Thus, for example, reference to a "sensor" includes one, two, or more sensors.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

Various aspects of the present disclosure can be illustrated by describing components that are coupled, attached, connected, and/or joined together. As used herein, the terms "coupled", "attached", "connected," and/or "joined" are used to indicate either a direct connection between two components or, where appropriate, an indirect connection to one another through intervening or intermediate components. In contrast, when a component is referred to as being "directly coupled", "directly attached", "directly connected," and/or "directly joined" to another component, no intervening elements are present or contemplated. Thus, as used herein, the terms "connection," "connected," and the like do not necessarily imply direct contact between the two or more elements. In addition, components that are coupled, attached, connected, and/or joined together are not necessarily (reversibly or permanently) secured to one another. For instance, coupling, attaching, connecting, and/or joining can comprise placing, positioning, and/or disposing the components together or otherwise adjacent in some implementations.

As used herein, directional and/or arbitrary terms, such as "top," "bottom," "front," "back," "left," "right," "up," "down," "upper," "lower," "inner," "outer," "internal," "external," "interior," "exterior," "proximal," "distal" and the like can be used solely to indicate relative directions and/or orientations and may not otherwise be intended to limit the scope of the disclosure, including the specification, invention, and/or claims.

Where possible, like numbering of elements have been used in various figures. In addition, similar elements and/or elements having similar functions may be designated by similar numbering. Furthermore, alternative configurations of a particular element may each include separate letters appended to the element number. Accordingly, an appended letter can be used to designate an alternative design, structure, function, implementation, and/or embodiment of an element or feature without an appended letter. Similarly, multiple instances of an element and or sub-elements of a parent element may each include separate letters appended to the element number. In each case, the element label may be used without an appended letter to generally refer to instances of the element or any one of the alternative elements. Element labels including an appended letter can be used to refer to a specific instance of the element or to distinguish or draw attention to multiple uses of the element. However, element labels including an appended letter are not meant to be limited to the specific and/or particular embodiment(s) in which they are illustrated. In other words, reference to a specific feature in relation to one embodiment should not be construed as being limited to applications only within said embodiment.

It will also be appreciated that where a range of values (e.g., less than, greater than, at least, and/or up to a certain value, and/or between two recited values) is disclosed or recited, any specific value or range of values falling within the disclosed range of values is likewise disclosed and contemplated herein.

It is also noted that systems, methods, apparatus, devices, products, processes, compositions, and/or kits, etc., according to certain embodiments of the present invention may include, incorporate, or otherwise comprise properties, features, aspects, steps, components, members, and/or elements described in other embodiments disclosed and/or described herein. Thus, reference to a specific feature, aspect, steps, component, member, element, etc. in relation to one embodiment should not be construed as being limited to applications only within the embodiment. In addition, reference to a specific benefit, advantage, problem, solution, method of use, etc. in relation to one embodiment should not be construed as being limited to applications only within said embodiment.

The headings used herein are for organizational purposes only and are not meant to be used to limit the scope of the description or the claims. To facilitate understanding, like reference numerals have been used, where possible, to designate like elements common to the figures.

Some abbreviations that may be used in the description below include:

| | |
|---|---|
| FU | Follicular Unit |
| HCI | High Capacity Implanter |
| HCI-3 | HCI with 3 needles configuration |
| NAL | Needle Adjust/Locker |
| NB | Needle Base |
| NGS | Needle Guide/Stop |
| NH | Needle Holder |
| PB | Piston Base |
| SS | Stainless Steel |

An embodiment of the invention, as shown and described by the various figures and accompanying text provides a High Capacity Implanter (HCI), a medical device developed to allow the implantation of multiple Follicular Units (FU) during a hair implant surgery. The HCI is a hair implanter capable of implanting multiple FUs in the patients' scalp. It has been tested, for example, under 3 and 5 needle configurations and exhibits compliance with its target to provide the multi-hair implantation at a single application thereby reducing the hair implant surgery cycle time.

With initial reference to FIGS. 1A-1D and FIG. 2, a high capacity implanter (HCI) 10 in a 3-needle configuration (HCI-3) will now be described. As will be described in greater detail below, the inventive features provide for the configuration of 3 or more needles in a single implanting instrument. The HCI-3 was designed to allow the implantation of 3 follicular units (FU) in a single application at a time. FIG. 1A is a side view of the HCI, FIG. 1B is a bottom view, FIG. 1C is a top view, and FIG. 1D is a perspective view of the HCI.

The HCI 10 is a hair follicle implant instrument or tool for implanting FUs (aka hair follicles) into skin. The HCI 10 includes a needle holding assembly 11 configured to hold a plurality of needles 14 which includes at least three implant needles as discussed above, in a staggered arrangement (also referred to as a zig-zag pattern or configuration). The needle holding assembly 11 includes a needle base 12 configured to hold the plurality of needles in the staggered arrangement, and a needle holder 13 configured to hold the needle base 12 and to be held by a hair follicle implant surgeon, during implantation, in a fixed position.

A needle guide 15 is slidably coupled to the needle holding assembly 11. The needle guide 15 is configured to provide a skin stop surface 16 while guiding the plurality of needles 14 in the staggered arrangement during implantation of FUs into the skin. A plurality of pistons 17, e.g. three or more pistons, are configured to slide within a respective one of the plurality of needles 14 and hold a corresponding FU in the skin while the plurality of needles 14 is retracted from the skin. A piston base 18 is slidably coupled to the needle holding assembly 11. The piston base 18 is configured to hold the pistons 17 in a corresponding staggered arrangement to slide within the plurality of needles 14 when actuated during implantation of FUs into the skin.

A spring 19 (e.g. a coil spring) is carried between the needle holding assembly 11 and the piston base 18. The spring 19 is configured to bias the piston base 18 in a retracted position. The spring 19 is offset from a central axis A of the piston base 18, and the needle holder 13 holds the plurality of needles in the staggered arrangement also offset from the central axis A of the piston base 18, as will be described in greater detail below. The hair follicle implant surgeon grips the needle holder 13 during implantation, in a fixed position, with the needle guide 15 being slidably actuated relative to the needle holder 13 via the piston base 18 which acts as a plunger.

A needle adjustment device 20 is carried by the piston base 18. The needle adjustment device 20 is configured to adjustably couple the piston base 18 to the needle guide 15 for simultaneous movement relative to the needle holding assembly 11 during implantation. The needle guide 15 may include an adjustment interface 21, at an opposite end from the skin stop surface 16 and is configured to engage the needle adjustment device 20. The adjustment device 20 and the adjustment interface 21 together define a quick-release mechanism of the needle holding assembly 11 and configured to provide for the removal and installation of the needle base 12 from/on the needle holder 13.

Figure 3:
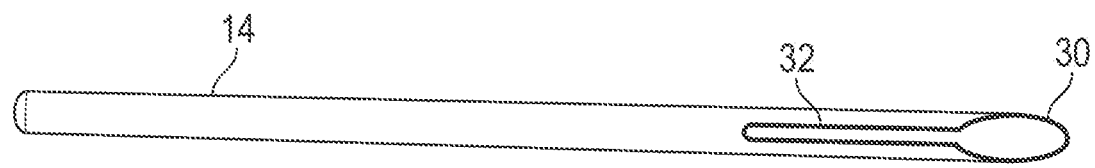
FIG. 3 is a top view of an example of a needle for the HCI of FIGS. 1A-1D.

Referring additionally to FIG. 3, the needles 14 are made of stainless steel (SS) and have a sharp end cut 30 that allows the insertion of the FU in a FU channel 32 allowing the FU to go inside the skin along with the needle insertion. FIG. 3 illustrates a single needle 14 with the FU channel 32 as a reference.

Figure 4A:
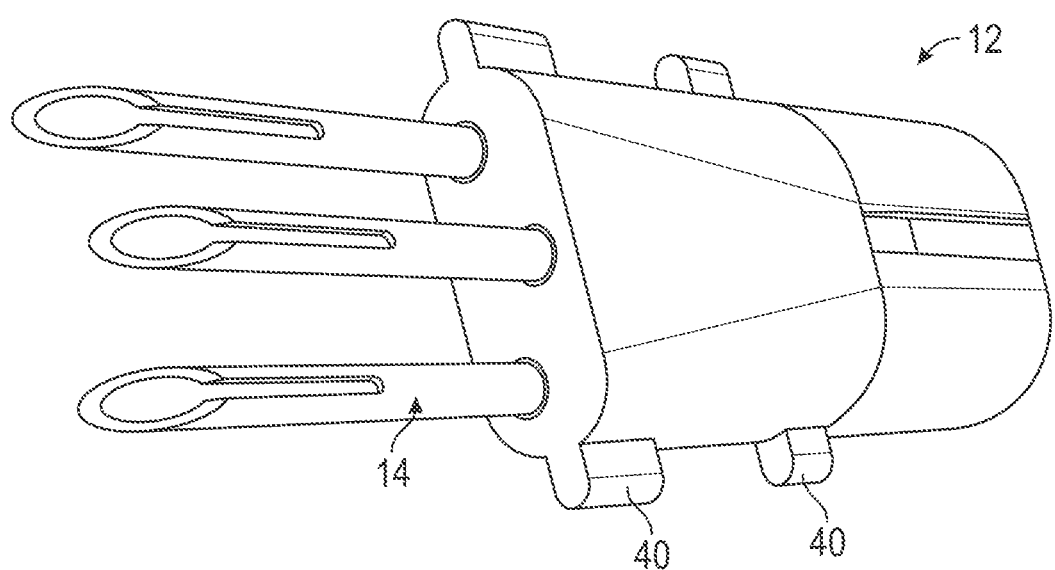
FIG. 4A is a perspective view of an example of a needle base for the HCI of FIGS. 1A-D.
Figures 4B, 4C, 4D:
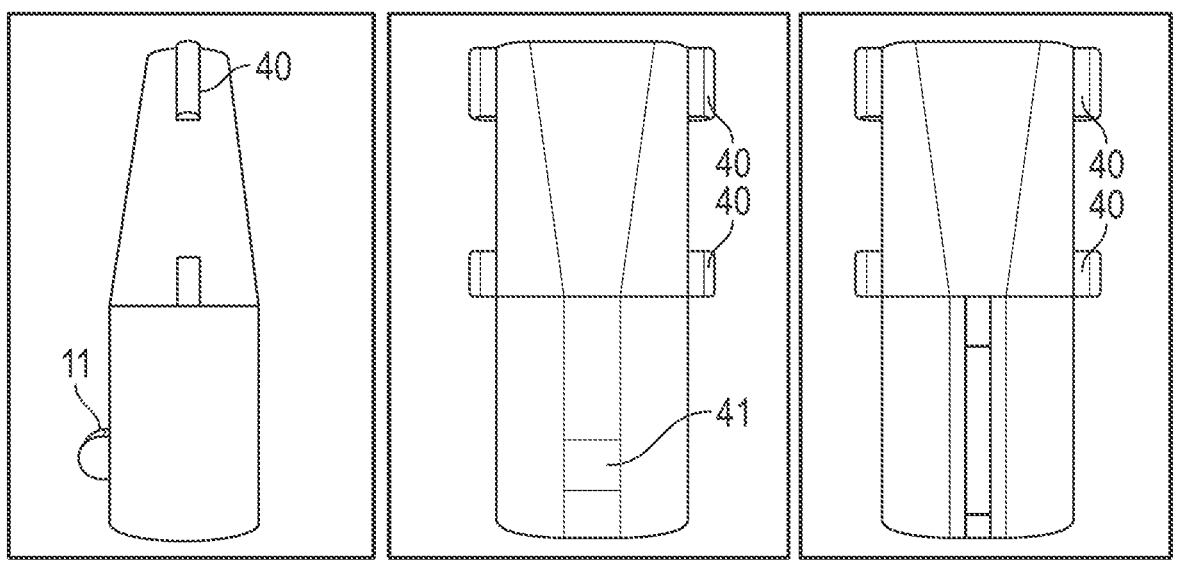
FIG. 4B is a side view of the needle base FIG. 4A.
FIG. 4C is a bottom view of the needle base FIG. 4A.
FIG. 4D is a top view of the needle base FIG. 4A.

FIG. 4A is a perspective view of an example of the needle base 12 for the HCI 10 of FIGS. 1A-1D. FIG. 4B is a side view, FIG. 4C is a bottom view, FIG. 4D is a top view, FIG.

Figures 4E, 4F:
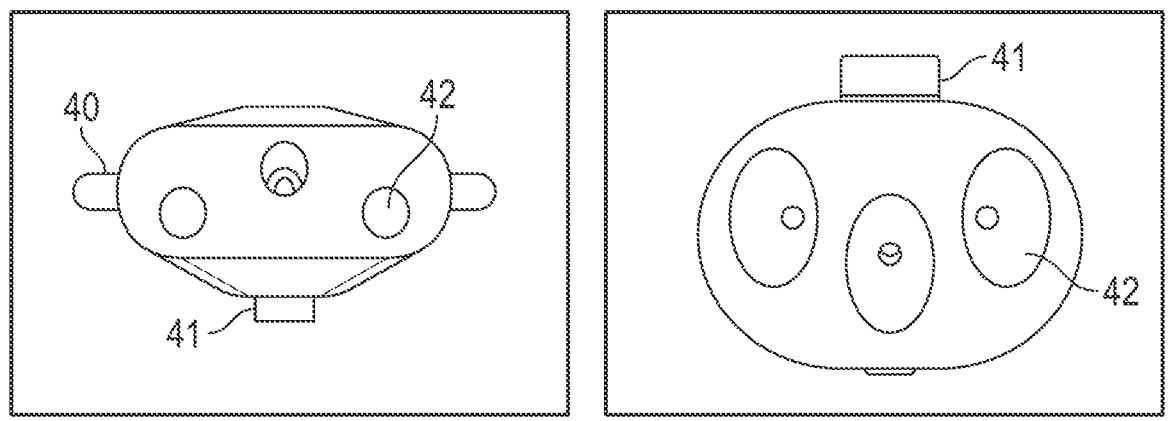
FIG. 4E is a front view of the needle base FIG. 4A.
FIG. 4F is a rear view of the needle base FIG. 4A.
Figure 5A:
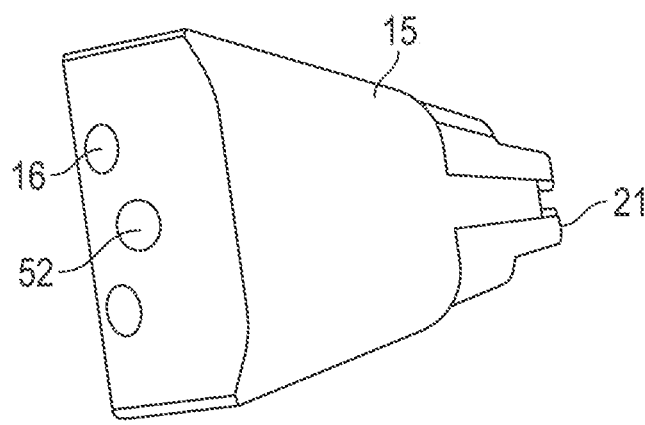
FIG. 5A is a perspective view of an example of a needle guide for the HCI of FIGS. 1A-D.
Figure 5B:
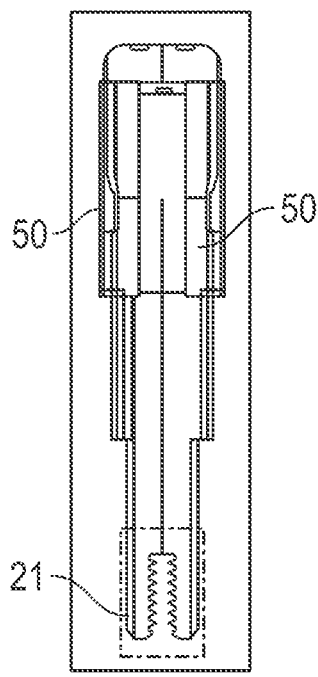
FIG. 5B is a bottom view of the needle guide FIG. 5A.
Figure 5C:
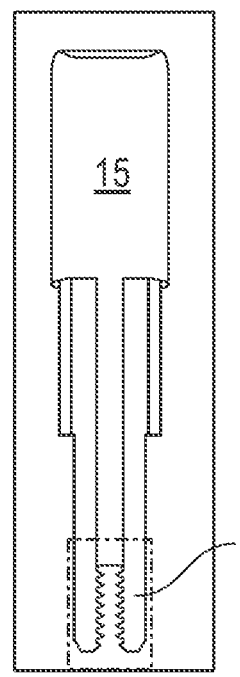
FIG. 5C is a top view of the needle guide FIG. 5A.
Figure 5D:
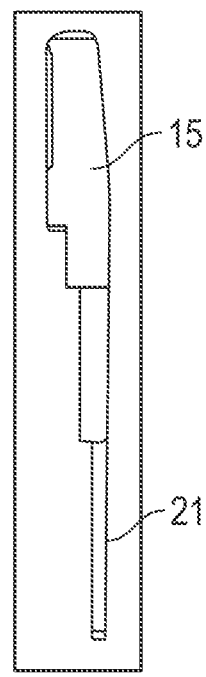
FIG. 5D is a side view of the needle guide FIG. 5A.

4E is a front view, and FIG. 4F is a rear view of the needle base 12. As illustrated, the needle base 12 includes a plurality of guide members 40. The guide members 40 interface with guide rails 50 (FIGS. 5B and 5F) on the needle guide 15 to guide relative movement therebetween. The needle base 12 includes a locking member 41 configured to lock the needle base 12 to the needle holder 13 and prevent relative movement therebetween during implantation.

The needle base 12 includes piston passages 42 therein configured to permit passage of each piston 17 within the corresponding needle 14. As illustrated, the piston passages 42 are elliptical cone passages. With specific reference to FIGS. 4E and 4F, the piston passages 42 are illustratively provided by holes that allow the passage of the pistons 17 within the needle base 12 and within each needle 14. To allow an easier insertion of the pistons 17 during the change of needles 14, the piston passages 42 of the needle base 12 have a larger and elliptical cone shape at the rear (FIG. 4F) which then decreases along the axis to a circular cone shape and a circular opening (FIG. 4E) that secures the needles 14 and allows the passage of the piston 17.

The needle base 12 may be plastic part with the function of holding the 3 needles together with a specific configuration referred to herein as staggered or zig-zag. This configuration prevents the needles 14 from cutting into the patient scalp all at once, since the first 2 "bottom needles" go in to the skin before the "upper needle", diminishing the pressure over the skin that could result in the "previously implanted FUs" being expelled, for example, due to the pressure caused in the skin by the multiple needles going inside the skin simultaneously (also referred to as "popping"). The staggered configuration also allows the needles 14 to be closer to each other (as a result of the diminished pressure), improving the quality on the hair implantation coverage area.

Figure 14:
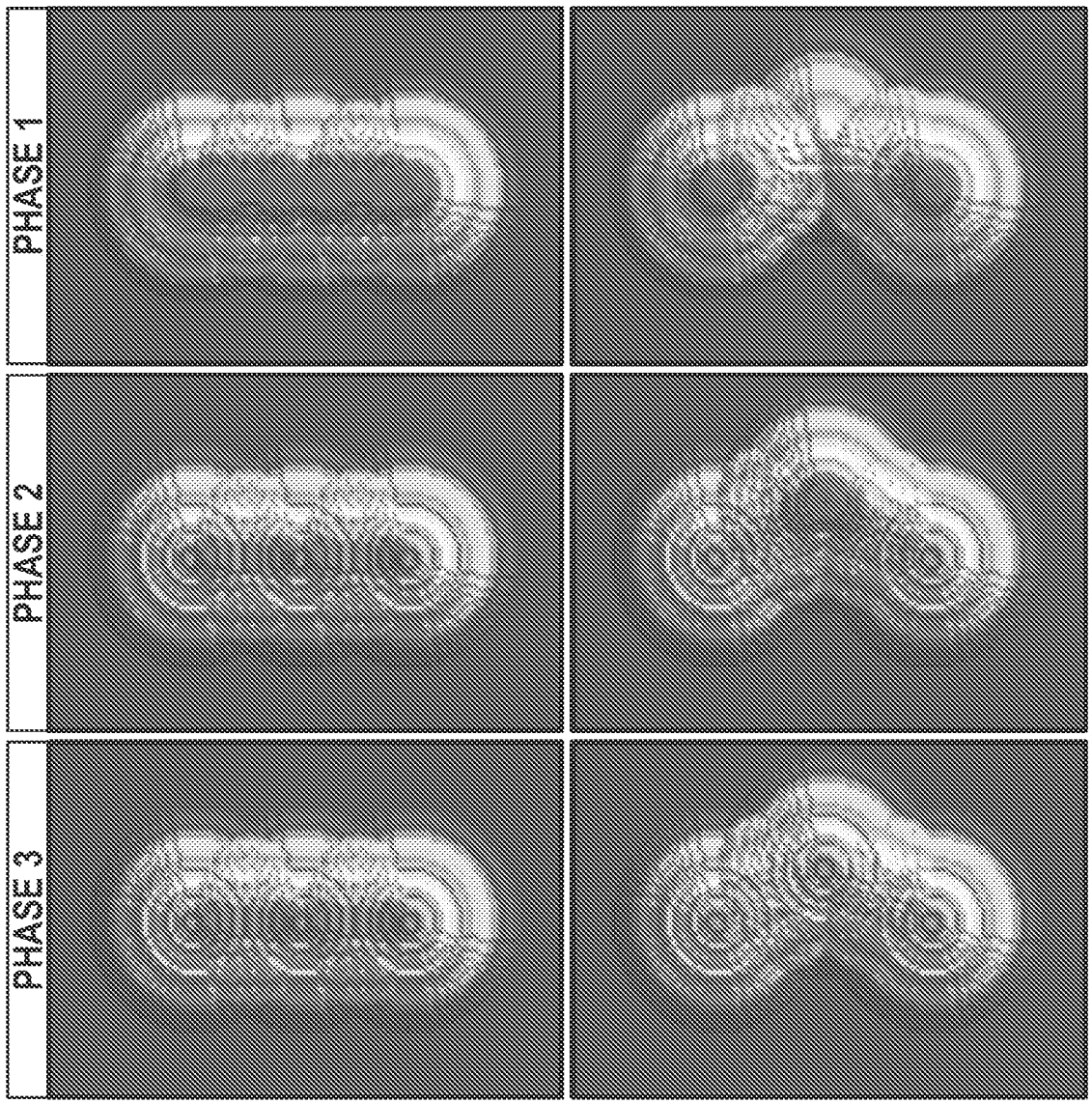
FIG. 14 is a display of a skin stress simulation comparing an inline multi-needle implanter versus the staggered needle arrangement for the HCI of FIGS. 1A-1D during PHASES 1-3 of FU implantation.

With additional reference to FIG. 14, the advantages of the staggered configuration will be discussed in further detail. FIG. 14 is a display of a skin stress simulation comparing an inline multi-needle implanter (left side images) versus the staggered needle arrangement (right side images) for the HCI 10 of FIGS. 1A-1D during PHASES 1-3 of FU implantation. As shown, the numeric simulation of the needles "in line" versus "staggered" needles going inside the skin indicates that the skin stress level is more uniform or even in the staggered configuration compared to the "in line" configuration.

A goal of the HCI 10 is to provide the desired coverage and density results. The coverage is related to needle spacing, and it is preferable that the needles 14 are close to each other trying to respect the spacing the surgeons would follow during surgery. In the case of the HCI 10, a center-to-center needle spacing of 2.7 mm was used, for example, during various tests. Of course, other spacings (e.g. decreased spacing) are also contemplated in view of the staggered arrangement and the off-center spring arrangement. To avoid FU popping, the inventive embodiments use the staggered or zig-zag distribution of the needles to prevent the two nearest needles from entering the skin simultaneously. The staggered distribution allows the pressure in the skin to be as close as possible to a single needle insertion, since the staggered design allows the needle to be inserted in phases as shown in FIG. 14. It is important to note that for the needles to go into the skin in phases, a 60° angle of insertion is preferred, and was used for the present embodiments of the HCI 10 prototypes and for the simulation in FIG. 14.

Figure 5E:
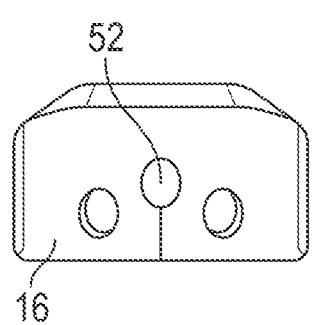
FIG. 5E is a front view of the needle guide FIG. 5A.
Figure 5F:
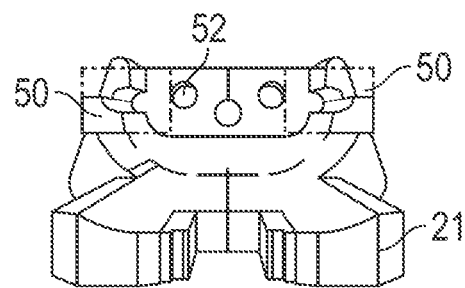
FIG. 5F is a rear view of the needle guide FIG. 5A.

With additional reference to FIGS. 5A-5F, features of the needle guide 15 will be described. The needle guide 15 includes the skin stop surface 16 and may be a plastic part that operates as a guide to the needles 14 and as a sliding guide to the needle base 12 during the HCI 10 operation. As such, the needle guide 15 operates as the interface between the HCI 10 and the patient scalp providing a stop area against the skin while the needles 14 are retracted thereby leaving the FUs in the skin. The guide rails 50 (FIGS. 5B and 5F) on the needle guide 15 interface with guide members 40 of the needle base 12 to guide relative movement therebetween. Needle passages 52 are also included in the needle guide 15 (e.g. as shown in FIGS. 5E and 5F) so that the needles 14 held by the needle base 12 may slidably pass-through the needle guide 15 during operation of the HCI 10.

The needle guide 15 with the aid of the needle adjustment device 20 controls the needle height to be customized per each patient's skin characteristics. As discussed above, the needle adjustment device 20 is carried by the piston base 18 and is configured to adjustably couple the piston base 18 to the needle guide 15 for simultaneous movement relative to the needle holding assembly 11 during FU implantation. As illustrated in FIGS. 5A-5F, the needle guide 15 includes an adjustment interface 21 at an opposite end from the skin stop surface 16. The adjustment interface is configured to engage the needle adjustment device 20 and allows with the simple pressing of the adjustment device 20 (aka a "release button") to adjust the needle height with 4 mm displacement in "steps" of 1 mm each, for example. The adjustment device 20 and the adjustment interface 21 together define a quick-release mechanism of the needle holding assembly 11 which is configured to provide for the removal and installation of the needle base 12 from/on the needle holder 13, for example, during a needle changing operation.

With additional reference to FIGS. 6A-6E, features of the needle holder 13 will be described. The needle holder 13 may be considered the main body of the HCI 10, and may be a plastic part designed for the surgeon to hold during the FU implantation operation. The needle holder 13 is responsible for holding the needle base 12 and together define the needle holder assembly 11. The needle holder 13 holds the needles 14 through the needle base 12, in a fixed position, while the needle holder assembly 11 moves relatively backward (e.g. sliding) with respect to the needle guide 15, pistons 17 and piston base 18 leaving the FUs inside the skin.

Figure 6A:
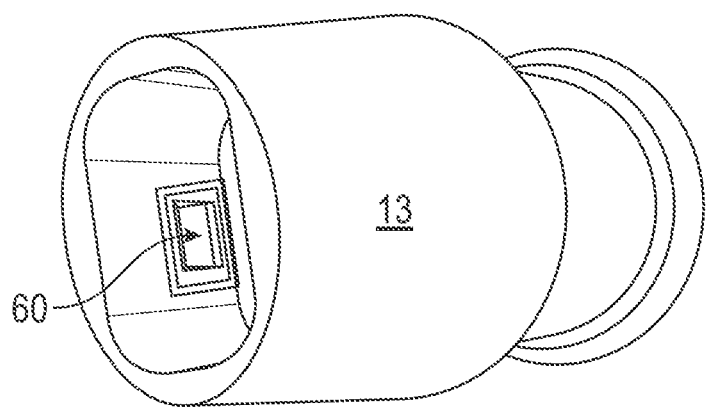
FIG. 6A is a perspective view of an example of a needle holder for the HCI of FIGS. 1A-D.
Figure 6B:
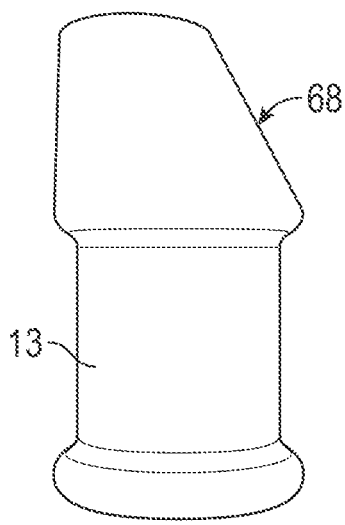
FIG. 6B is a side view of the needle holder FIG. 6A.
Figure 6C:
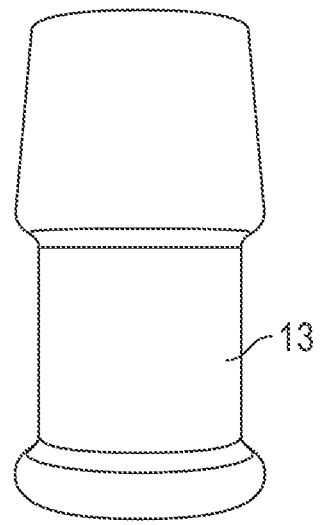
FIG. 6C is a top view of the needle holder FIG. 6A.
Figures 6D, 6E:
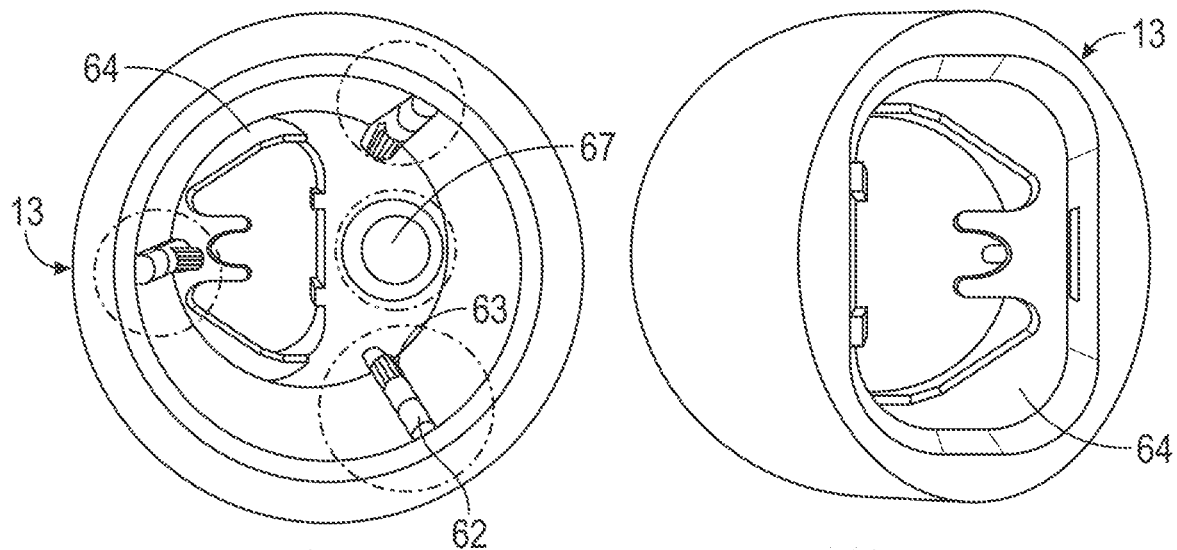
FIG. 6D is a rear view of the needle holder FIG. 6A.
FIG. 6E is a front view of the needle holder FIG. 6A.

Features of the needle holder 13 include a needle base slot 60 to fit the locking member 41 (e.g. bottom bulge in FIGS. 4B and 4C) of the needle base 12 to hold the needle base together therewith. Actuation rails 62 and associated bulges 63 are also included, as well as a piston base stop 64. In the inside diameter of the needle holder 13 there are 3 rails positioned to guide the piston base 18 while the HCI 10 is actuated. Along the 3 rails there are bulges 63 to prevent the piston base 18 from coming out of the HCI 10 (e.g. as best seen in FIG. 6D). In the bottom of this inside diameter there is a piston base stop 64 that holds the piston base 18 in its final position during its actuation.

A spring mounting bulge 67 is included to mount the coil spring 19 within the needle holder 13. As shown in FIG. 6D, the spring bulge 67 is off center within the needle holder 13 body. As illustrated in FIGS. 6B and 6C, the needle holder 3 includes a ramp surface 68 which further emphasizes the offset spring arrangement while the passage of the needles 14 and pistons 17 are not within the space delineated by the ramp surface 68.

An important feature of the needle holder 13 is the off-center spring actuation. The spring actuation is off-center (i.e., moved to the side) as well as the needles 14 which are moved to the opposite side. This off-center design allows the HCI 10 to include the needle base 12 design with the desired staggered configuration, for example, with any desired proximity or distribution configuration that the designer might need. Additionally, the off-center design avoids the use of long needles since there is no need for the needles to extend within the center of a spring, or surrounding the spring, for example, as in conventional implanters. This also provides a reduction in the amount of stainless-steel tubing being used as the needles 14 in the HCI 10 may be reduced in length to, for example, less than half the length of conventional implanter needles.

With additional reference to FIGS. 7A-7E, features of the piston base 18 will be described. The piston base 18 may be a plastic part designed to hold the pistons 17 and hold the needle guide 15 on the adjustment range (e.g. 4 mm range of adjustment) of the needle height. The main function of the piston base 18 may operate as an actuation button during the HCI operation (note flat button surface 71 in FIG. 7D).

Figure 7A:
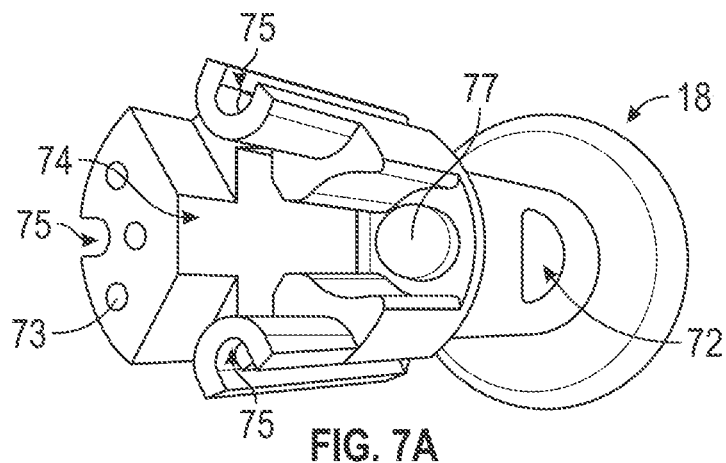
FIG. 7A is a perspective view of an example of a piston base for the HCI of FIGS. 1A-1D.
Figure 7B:
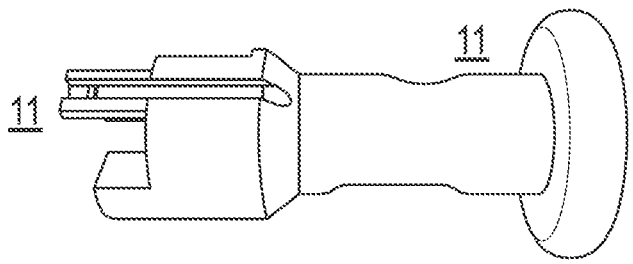
FIG. 7B is a side view of the piston base FIG. 7A.
Figure 7C:
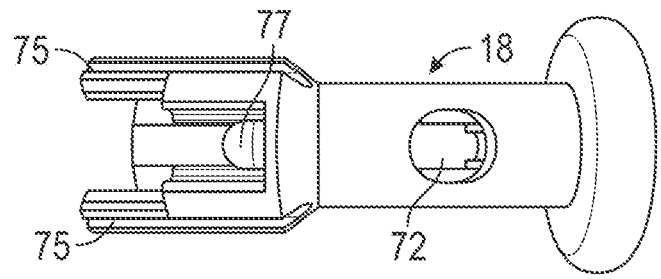
FIG. 7C is a top view of the piston base FIG. 7A.
Figure 7D:
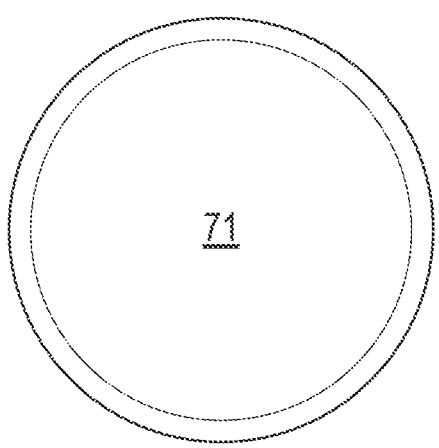
FIG. 7D is a rear view of the piston base FIG. 7A.
Figure 7E:
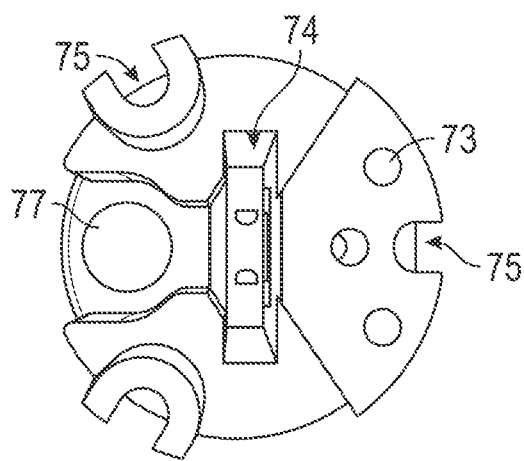
FIG. 7E is a front view of the piston base FIG. 7A.
Figure 9A:
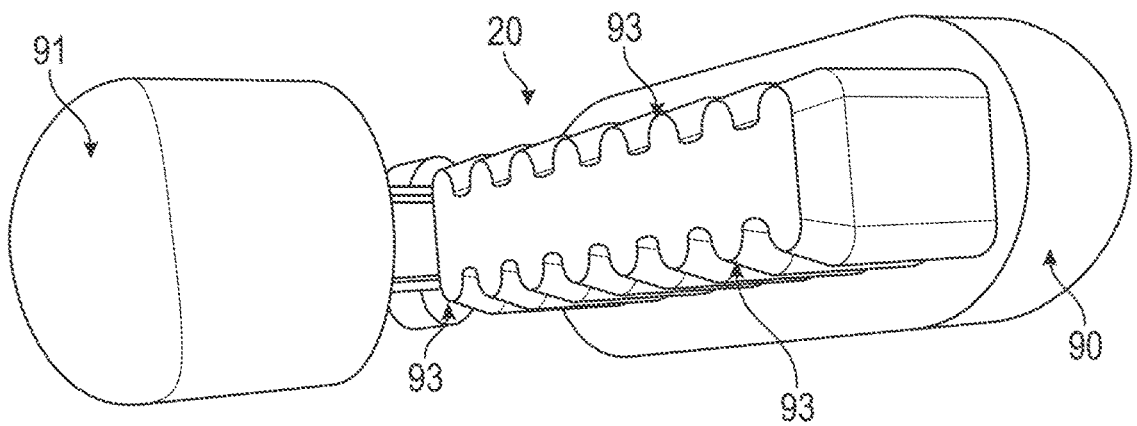
FIG. 9A is a perspective view of an example of a needle adjustment device for the HCI of FIGS. 1A-1D.
Figure 9B:
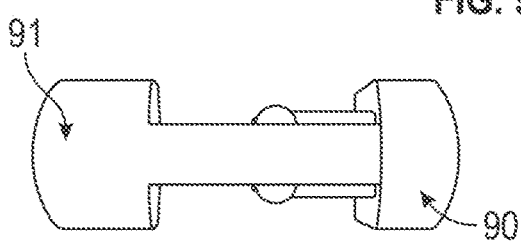
FIG. 9B is a rear view of the needle adjustment device FIG. 9A.
Figure 9C:
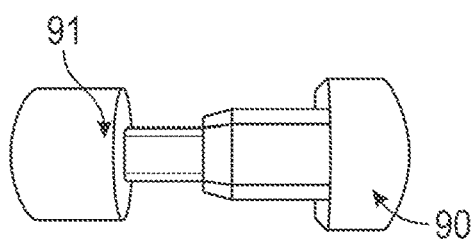
FIG. 9C is a front view of the needle adjustment device FIG. 9A.
Figure 9D:
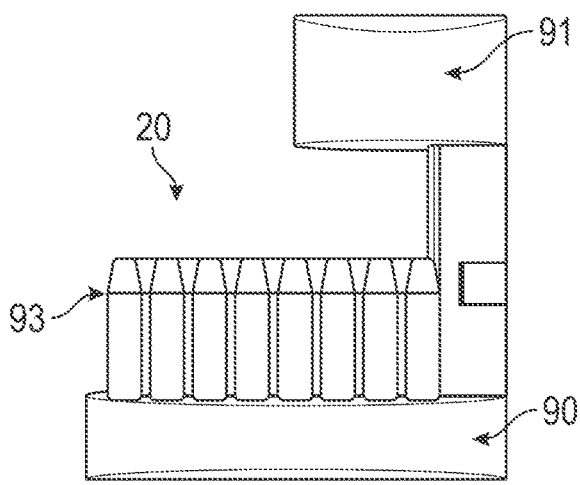
FIG. 9D is a side view of the needle adjustment device FIG. 9A.
Figure 9E:
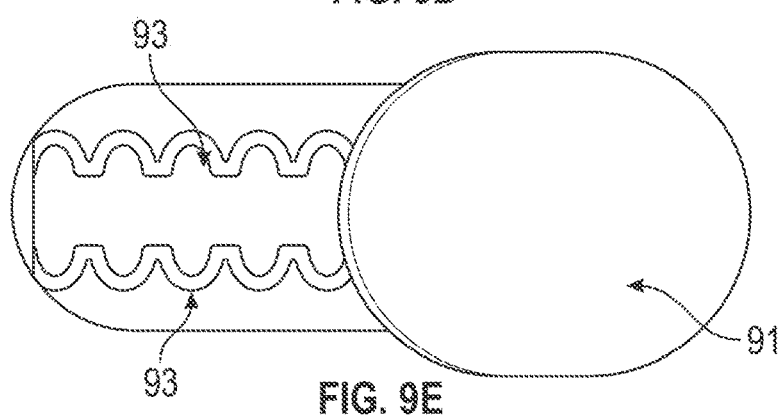
FIG. 9E is a top view of the needle adjustment device FIG. 9A.

A mounting hole 72 is included to mate with the needle adjustment device 20. Piston holes 73 (e.g. 3 piston holes as shown in FIGS. 7A and 7E) are included in an end face of the piston base 18. A channel 74 for the adjustment interface 21 of the needle guide 15 is included in a generally central position of the piston base 18. There are grooves 75 (e.g. three grooves 120 degrees from each other) for interfacing with the rails 62 of the needle holder 13. A spring knob 77 is included to position the other end of the coil spring 19.

With additional reference to FIGS. 8A and 8B, the pistons 17 are shown mounted to the piston base 18 and extending within the needles 14. The pistons 17 may be simply stainless-steel cylinders or rods that have the function of pushing or holding the FUs while the needles 14 are removed from the patient's skin. To do so, each of the pistons 17 (e.g. three pistons) slides inside each of the needles 14 and are attached to the piston base 18 at the piston holes 73, while the opposite ends 78 (or piston tips) may extend out of the needles 14 during implantation.

With additional reference to FIGS. 9A through 9E, features of the needle adjustment device 20 are described. The needle adjustment device 20 includes a lock button 90 and a release button 91. Teeth 93 are provided to engage with the adjustment interface 21 of the needle guide 15. The needle adjustment device 20 is carried by the piston base 18 and configured to adjustably couple the piston base 18 to the needle guide 15 for simultaneous movement relative to the needle holding assembly 11 during implantation. The adjustment interface 21 is configured to engage the teeth 93 of the needle adjustment device 20 and allows with the simple pressing of the adjustment device 20 release button 91 to adjust the needle height. The pressing of the lock button 90 will re-engage the teeth 93 with the adjustment interface 21 of the needle guide 15.

Thus, the needle adjustment device 20 may be viewed as an actuator responsible for locking the needle guide 15 in its position. When the release button 91 is pushed it allows the adjustment of the needle height in a 4 mm range of adjustment, for example, with 1 mm steps so that the needle can be adjusted to 10, 9, 8, 7 and 6 mm heights, for example. The needle adjustment device 20 also allows the quick change of the needles 14 when required through the quick removal of the needle guide 15 that then allows for the removal of the needle base 12, as will be described in detail below.

Figure 10A:
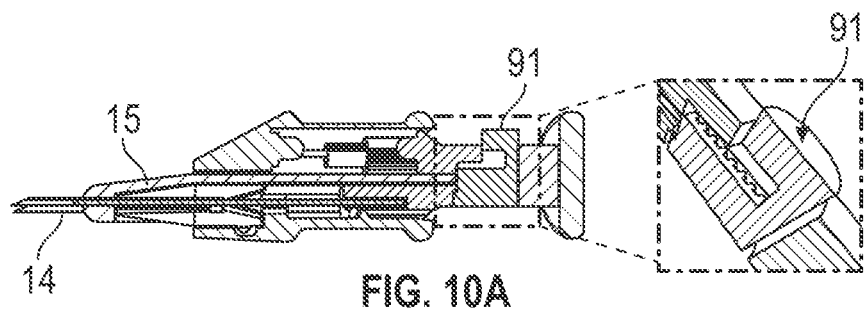
FIGS. 10A-10D are cross-sectional views illustrating the needle height adjustment for the HCI of FIGS. 1A-1D.
Figure 10B:
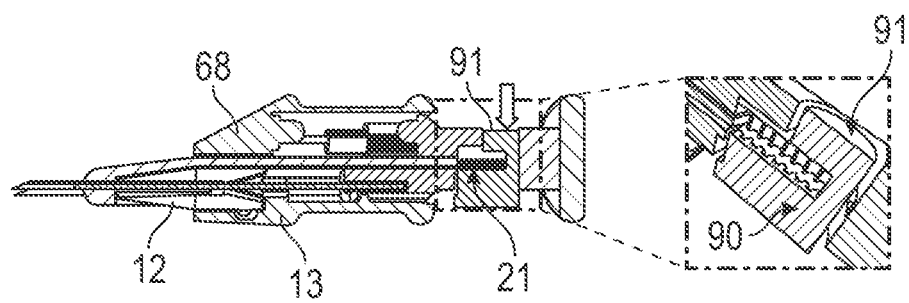
Figure 10C:
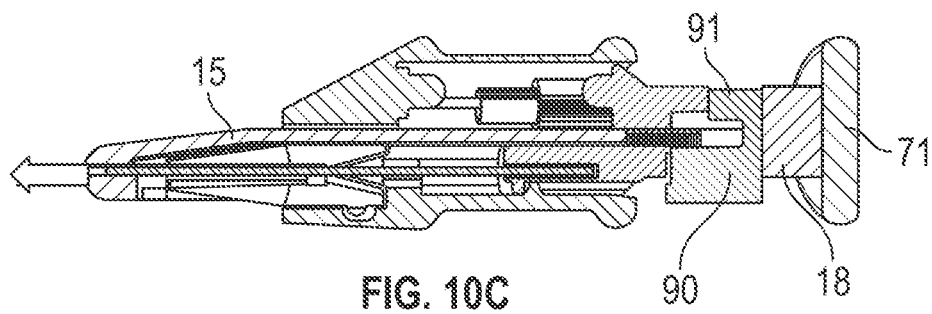
Figure 10D:
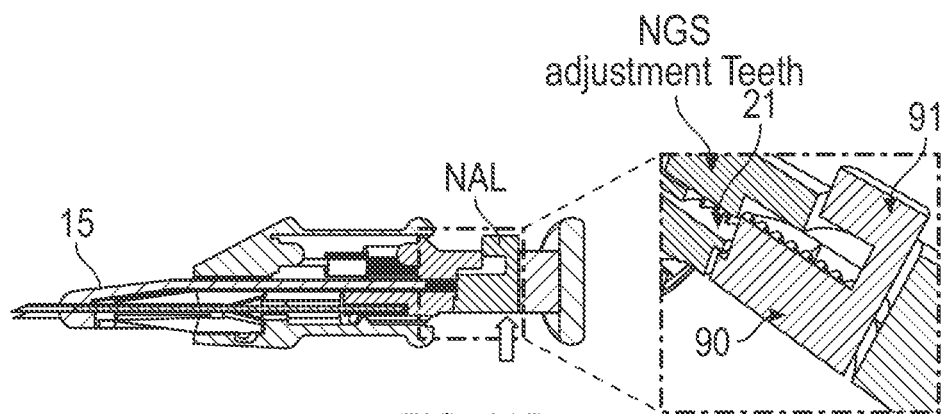

With additional reference to FIGS. 10A through 10D, the procedure to release the actuate the needled adjustment device 20 in order to adjust the needle height from 10 mm down to 6 mm will be described. FIGS. 10A-10D are cross-sectional views, including enlarged views, illustrating the needle height adjustment process for the HCI 10 of FIGS. 1A-1D. Beginning at FIG. 10A, the needle adjustment device 20 is locked at the 10 mm setting. The teeth 93 are engaged with corresponding interlocking members of the adjustment interface 21 of the needle guide 15. At FIG. 10B, when the release button 91 is depressed, the teeth 93 are released from coupling to the adjustment interface 21. The needle guide 15 is now freely movable or slidable in a direction away from the piston 18 to slide the needle guide 15 relative to the needle holder assembly 11 and thereby reduce the height of the needles 14 extending from the skin stop surface 16 of the needle guide 15. As shown in FIG. 10C, the needle height has been reduced from 10 mm to 6 mm, and in FIG. 10D the lock button 90 has been pressed to re-engage the teeth 93 with the adjustment interface 21 of the needle guide 15 thereby locking the needle height at 6 mm. Of course, other ranges and/or additional settings are within the scope of the invention, as would be appreciated by those skilled in the art.

With additional reference to FIGS. 11A through 11C, the FU implantation process using the HCI 10 (e.g. HCI-3 as shown) is described. In step 1 (FIG. 11A), FUs are inserted into the needle channels 32 of the needles 14 (the FUs are not shown as the details of a FU being provided in the needle 14 is known to the skilled artisan). Using a recommended angle of 60 degrees, in step 2, the needles 14 (carrying the FUs) are inserted into the patient's scalp (e.g. in the phases described with reference to FIG. 14). The pressure exerted by the staggered needle arrangement provides a more even distribution and avoids popping of FUs from their implantation locations. In step 3, the flat button surface 71 of the piston base 18 is pressed to actuate the pistons 17 through the needles 14 and remove the needles 14 from the scalp while leaving the FUs implanted therein. The surgeon would then return to step 1 and repeat until the surgery is complete and the desired coverage is achieved.

Figure 12A:
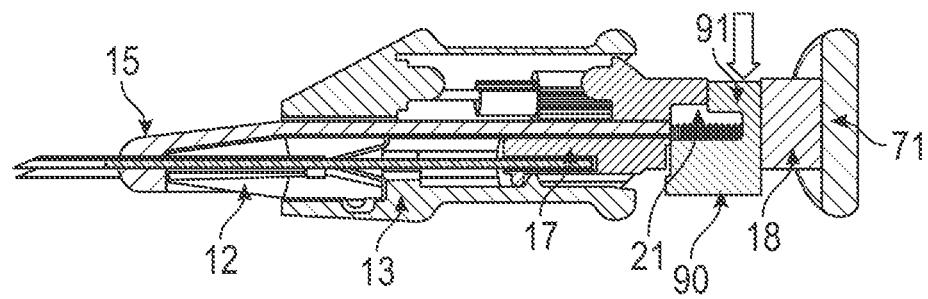
FIGS. 12A-12C are cross-sectional views illustrating the quick needle removal and installation features of the HCI of FIGS. 1A-1D.
Figure 12B:
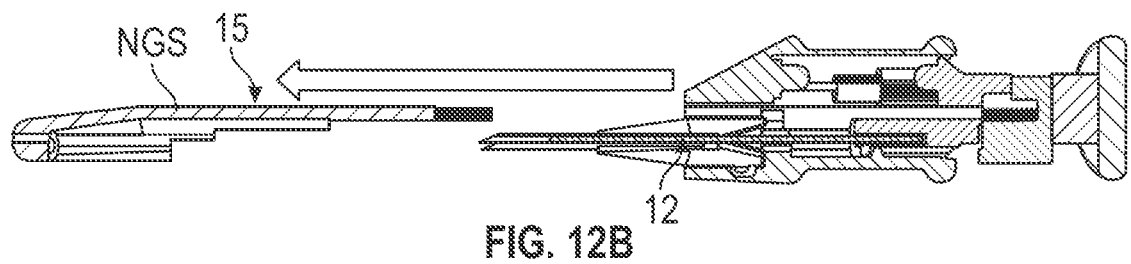
Figure 12C:
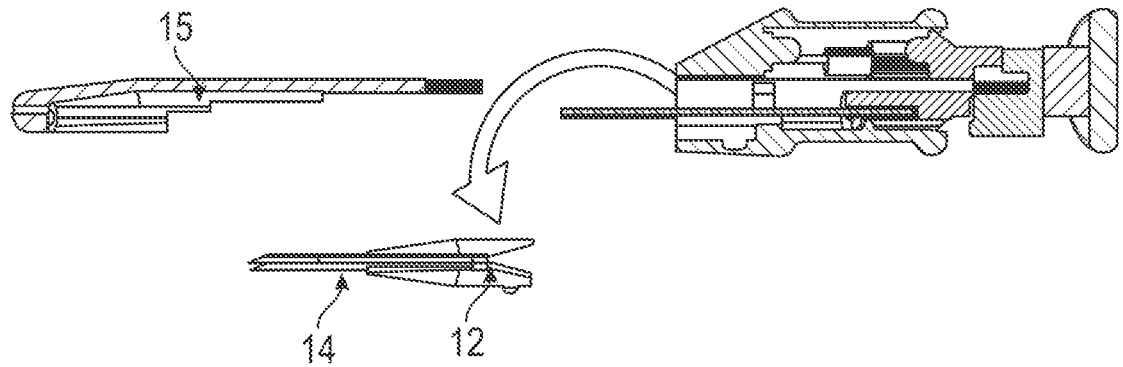

With reference to FIGS. 12A through 12C, a needle "quick change" will be described. As described, the quick change includes 6 general steps to quickly remove, install and adjust a new set of needles 14 and needle base 12 if necessary, during the surgery. At FIG. 12A (step 1), it can be seen that the release button 91 has been pressed down and the teeth 93 are released from coupling to the adjustment interface 21. The needle guide 15 is now freely movable or slidable in a direction away from the piston 18 to slide the needle guide 15 relative to the needle holder assembly 11, and the technician may thereby remove the needle guide 15 from coupling with the needle holder assembly 11 (step 2). At step 3 (FIG. 12C), the needle base 12 and needles 14 are removed from the needle holder 13. Step 4 includes the new needles 14 and needle base 12 being reinstalled to the needle holder 13 (i.e., reverse of step 3). Step 5 includes the needle guide 15 being reinstalled to the needle holder assembly 11 (i.e., reverse of step 2). Step 6 includes locking the position and height of the needles 14 by pressing the locking button 90 to re-engage the teeth 93 of the adjustment interface device 20 with the adjustment interface 21 of the needle guide 15. The HCI 10 is now ready to use. The use of the release button 90 and lock button 91 provided by the adjustment interface device 20, allows the quick needle change and adjustment. Known implanters in the market may use a threaded interface to remove and adjust the needles, and the needle change can take approximately 1 min or longer. The relatively quick change using the HCI 10 may take around 10 to 15 seconds.

Figure 13A:
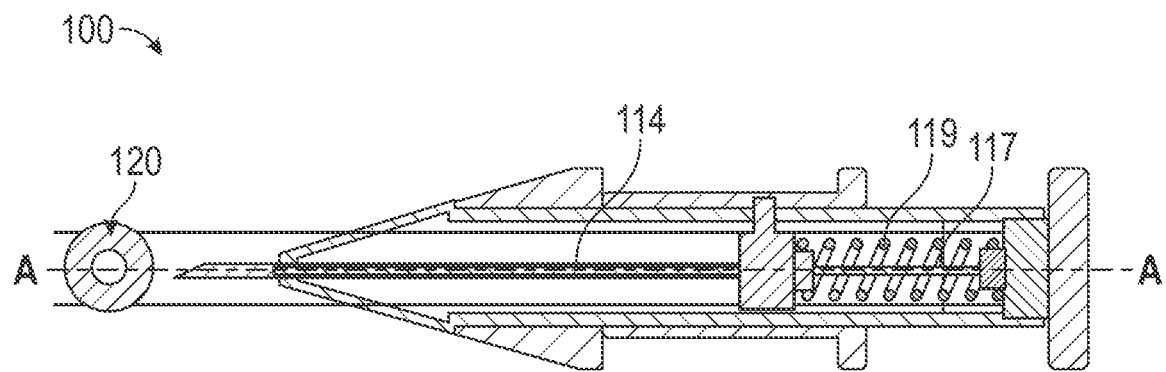
FIG. 13A is a cross-sectional view of a typical implanter illustrating the interference of the spring with needle arrangement according to the prior art.
Figure 13B:
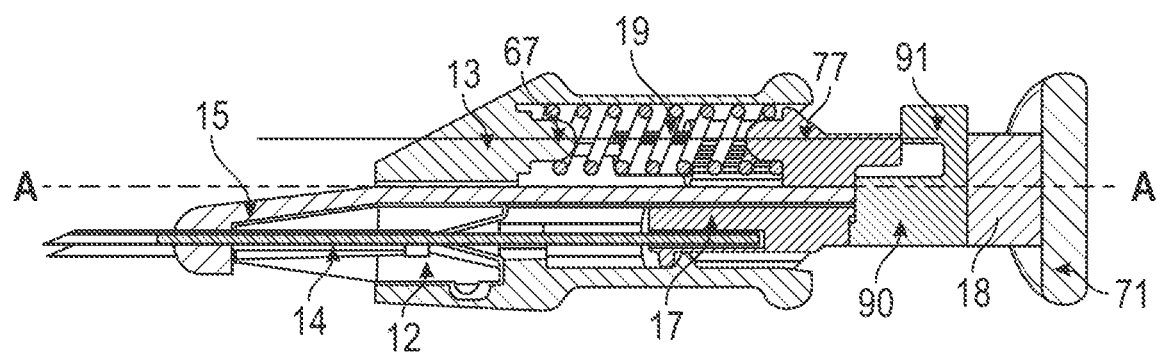
FIG. 13B is a cross-sectional view of the HCI of FIGS. 1A-1D and illustrating the off-center spring and needle arrangement according to the present invention, leaving the needle arrangement free of any possible interference with the spring.

With additional reference to FIGS. 13A and 13B, the advantages of the off-center needle and spring arrangement are described. FIG. 13A is a cross-sectional view of a typical implanter illustrating the interference of the spring with needle arrangement according to the prior art. In the known arrangement implanter 100, the single needle 114 and piston 117 share a centerline A with the spring 119. The annulus 120 illustrates a zone of interference including a margin to avoid spring scraping, where the spring limits the possibilities for multi-needle arrangements. Arrangements where the needles 114 and pistons 117 are centered would cause multiple needles to have a larger distance between them since the needle and pistons would have to keep some clearance from the spring 119 in order to properly operate without the spring scraping the cylinders.

FIG. 13B is a cross-sectional view of the HCI 10 of FIGS. 1A-1D and illustrating the off-center spring and needle arrangement according to the present invention. Here, the offset needles 14 and pistons 17 relationship allows a staggered arrangement (and other various arrangements) not provided for by the typical known implanters.

Embodiments of the present invention are also related to a method of making a hair follicle implant instrument HCI 10 for implanting hair follicles into skin. The method includes: providing a needle holding assembly 11 to hold a plurality of needles 14, including at least three implant needles, in a staggered arrangement; slidably coupling a needle guide 15 to the needle holding assembly 11, the needle guide 15 providing a skin stop surface 16 while guiding the plurality needles 14 in the staggered arrangement during implantation of hair follicles into the skin; sliding a plurality of pistons 17, comprising at least three pistons, into each one of the plurality of needles 14 to hold a corresponding hair follicle in the skin while the plurality of needles 14 is retracted from the skin; holding the pistons 17 with a piston base 18 in a corresponding staggered arrangement, and slidably coupling the piston base 18 to the needle holding assembly 11 so that the pistons 17 slide within the plurality of needles 14 when actuated during implantation of hair follicles into the skin; and biasing the piston base 18 in a retracted position with a spring 19 carried between the needle holding assembly 11 and the piston base 18, wherein the spring 19 is offset from a central axis A of the piston base; wherein the needle holder assembly 11 holds the plurality of needles 14 in the staggered arrangement offset from the central axis A of the piston base 18.

The instrument, HCI 10, described herein, can also be used in a pre-implant multi-incision modality. During follicular unit extraction, the surgeon extracts each follicle, e.g. with a pair of tweezers. The FUs may be placed on a dish. A plurality of incisions (e.g. 1 mm holes) may be created in the scalp using the HCI 10 without FUs positioned in the channels 32. In a subsequent step, the hair follicle is then implanted into these incisions. As the process is continued, depending on the number of grafts that the patient requires, the multi-needle HCI 10 may reduce more than 60% of the time used for pre-implant incisions minimizing the time the FUs are "out of the skin" and improving the survivability of the FUs after implantation.

Referring additionally to FIGS. 15A and 15B, alternative embodiments for use in the pre-implant multi-incision modality will be described. FIG. 15A is a perspective view of a high capacity instrument 150A that includes three needles in the staggered arrangement. FIG. 15B is a perspective view of a high capacity instrument 150B that includes five needles in the staggered arrangement. The high capacity instruments 150A/150B include needle holder assembly 151 to hold the plurality of needles 154 in the staggered arrangement. A skin stop surface 156 provides a stopping point for the surgeon if needed. The needle holder assembly 151 is coupled to an instrument base 158 to be held by the surgeon. The pressure exerted by the staggered needle arrangement provides a more even distribution as in the above described embodiments. This distribution of pressure may be important for patients with skin and scalp characteristics that are not optimal for direct incision and simultaneous follicular unit implantation. These embodiments increase the rate of incisions, reduce overall surgery time, while also minimizing trauma to the scalp.

Some of the illustrative aspects of the present invention may be advantageous in solving the problems herein described and other problems not discussed which are discoverable by a skilled artisan.

The present invention may have also been described, at least in part, in terms of one or more embodiments. An embodiment of the present invention is used herein to illustrate the present invention, an aspect thereof, a feature thereof, a concept thereof, and/or an example thereof. A physical embodiment of an apparatus, an article of manufacture, a machine, and/or of a process that embodies the present invention may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

The above description provides specific details, such as material types and processing conditions to provide a thorough description of example embodiments. However, a person of ordinary skill in the art would understand that the embodiments may be practiced without using these specific details.

Some of the illustrative aspects of the present invention may be advantageous in solving the problems herein described and other problems not discussed which are discoverable by a skilled artisan. While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced items. Thus, the scope of the invention should be determined by the appended claims and their legal equivalents, and not by the examples given.

The invention claimed is:

1. A hair follicle implant instrument for implanting hair follicles into skin, the hair follicle implant instrument comprising:
   a needle holding assembly configured to hold a plurality of needles, including at least three implant needles, in a staggered arrangement;
   a needle guide, slidably coupled to the needle holding assembly, and configured to provide a skin stop surface while guiding the plurality of needles in the staggered arrangement during implantation of hair follicles into the skin;
   a plurality of pistons, comprising at least three pistons, each piston configured to slide within a respective one of the plurality of needles and hold a corresponding hair follicle in the skin while the plurality of needles is retracted from the skin;
   a piston base, slidably coupled to the needle holding assembly, and configured to hold the plurality of pistons in a corresponding staggered arrangement to slide within the plurality of needles when actuated during implantation of hair follicles into the skin; and
   a spring carried between the needle holding assembly and the piston base, and configured to bias the piston base in a retracted position, wherein the spring is offset from a central axis of the piston base and is also spaced apart and offset from the pistons;
   wherein the needle holding assembly holds the plurality of needles in the staggered arrangement offset from the central axis of the piston base.

2. The hair follicle implant instrument of claim 1, wherein the needle holding assembly comprises:
   a needle base configured to hold the plurality of needles in the staggered arrangement; and
   a needle holder configured to hold the needle base during implantation in a fixed position with the needle guide being slidably actuated relative thereto via the piston base.

3. The hair follicle implant instrument of claim 2, wherein the needle base includes piston passages therein configured to permit passage of each piston within the corresponding needle.

4. The hair follicle implant instrument of claim 3 wherein the piston passages comprise elliptical cone passages.

5. The hair follicle implant instrument of claim 2, wherein the needle base includes at least one guide member; and wherein the needle guide includes at least one guide rail configured to interface with the at least one guide member of the needle base and guide relative movement therebetween.

6. The hair follicle implant instrument of claim 2, wherein the needle base includes a locking member configured to lock the needle base to the needle holder and prevent relative movement therebetween during implantation.

7. The hair follicle implant instrument of claim 1, further comprising a needle adjustment device, carried by the piston base, and configured to adjustably couple the piston base to the needle guide for simultaneous movement relative to the needle holding assembly during implantation.

8. The hair follicle implant instrument of claim 7, wherein the needle guide includes an adjustment interface at an opposite end from the skin stop surface; and wherein the needle guide is configured to engage the needle adjustment device.

9. The hair follicle implant instrument of claim 8, wherein the needle adjustment device and the adjustment interface together define a quick-release mechanism configured to provide for the removal from, and installation on, the needle holder.

10. A method of making a hair follicle implant instrument for implanting hair follicles into skin, the method comprising:
    providing a needle holding assembly to hold a plurality of needles, including at least three implant needles, in a staggered arrangement;
    slidably coupling a needle guide to the needle holding assembly, the needle guide providing a skin stop surface while guiding the plurality of needles in the staggered arrangement during implantation of hair follicles into the skin;
    sliding a plurality of pistons, comprising at least three pistons, into the respective plurality of needles to hold a corresponding hair follicle in the skin while the plurality of needles is retracted from the skin;
    holding the plurality of pistons with a piston base in a corresponding staggered arrangement, and slidably coupling the piston base to the needle holding assembly so that the plurality of pistons slide within the respective plurality of needles when actuated during implantation of hair follicles into the skin; and
    biasing the piston base in a retracted position with a spring carried between the needle holding assembly and the piston base, wherein the spring is offset from a central axis of the piston base and is also spaced apart and offset from the pistons;
    wherein the needle holding assembly holds the plurality of needles in the staggered arrangement offset from the central axis of the piston base.

11. The method of claim 10, wherein the needle holding assembly comprises:
    a needle base configured to hold the plurality of needles in the staggered arrangement; and
    a needle holder configured to hold the needle base during implantation in a fixed position; wherein the needle guide is slidably actuated relative thereto via the piston base.

12. The method of claim 11, wherein the needle base includes piston passages therein configured to permit passage of each piston within the corresponding needle.

13. The method of claim 12, wherein the piston passages comprise elliptical cone piston passages.

14. The method of claim 11, wherein the needle base includes at least one guide member; and wherein the needle guide includes at least one guide rail configured to interface with the at least one guide member of the needle base and guide relative movement therebetween.

15. The method of claim 11, wherein the needle base includes a locking member configured to lock the needle base to the needle holder and prevent relative movement therebetween during implantation.

16. The method of claim 10, further comprising providing a needle adjustment device, carried by the piston base, to adjustably couple the piston base to the needle guide for simultaneous movement relative to the needle holding assembly during implantation.

17. The method of claim 16, wherein needle guide includes an adjustment interface, at an opposite end from the skin stop surface, and configured to engage the needle adjustment device.

18. The method of claim 17, wherein the adjustment device and the adjustment interface together define a quick-release mechanism configured to provide for the removal from, and installation on, the needle holder.

19. A hair follicle implant instrument comprising:
- a needle holding assembly configured to hold a plurality of needles and comprising:
    - a needle base configured to hold the plurality of needles in the staggered arrangement, and
    - a needle holder configured to hold the needle base in a fixed position,
    - wherein the plurality of needles are implantable into skin, and
    - wherein the needle base includes a locking member configured to lock the needle base to the needle holder and prevent relative movement therebetween;
- a needle guide slidably coupled to the needle holding assembly, and configured to provide a skin stop surface, the needle base comprising at least one guide member, wherein the needle guide includes at least one guide rail configured to interface with the at least one guide member of the needle base and guide relative movement therebetween;
- a plurality of pistons, each configured to slide within a respective one of the plurality of needles, and hold a corresponding hair follicle;
- a piston base slidably coupled to the needle holding assembly and configured to hold the plurality of pistons to slide within the plurality of needles when actuated;
- a spring carried between the needle holding assembly and the piston base, the spring being configured to bias the piston base in a retracted position; and
- a needle adjustment device, carried by the piston base and configured to adjustably couple the piston base to the needle guide for simultaneous movement relative to the needle holding assembly;
- wherein the spring is offset from a central axis of the piston base and is also spaced apart and offset from the pistons;
- wherein the needle holding assembly holds the plurality of needles offset from the central axis of the piston base;
- wherein the needle guide is slidably actuated relative to the needle holder via the piston base.

20. The hair follicle implant instrument of claim 19, wherein the needle guide includes an adjustment interface at an opposite end from the skin stop surface; wherein the needle guide is configured to engage the needle adjustment device; and wherein the needle adjustment device and the adjustment interface together define a quick-release mechanism configured to provide for the removal from, and installation on, the needle holder.

* * * * *